US010010476B2

(12) United States Patent
Pearson et al.

(10) Patent No.: US 10,010,476 B2
(45) **Date of Patent: *Jul. 3, 2018**

(54) FEMALE SEXUAL STIMULATION DEVICE

(71) Applicants: Christine Pearson, Orlando, FL (US); Ralph Cuccuro, Jr., Orlando, FL (US)

(72) Inventors: Christine Pearson, Orlando, FL (US); Ralph Cuccuro, Jr., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,196

(22) Filed: May 5, 2017

(65) Prior Publication Data

US 2017/0239135 A1 Aug. 24, 2017

Related U.S. Application Data

(63) Continuation of application No. 14/713,600, filed on May 15, 2015, now Pat. No. 9,668,934.

(51) Int. Cl.
*A61F 5/00* (2006.01)
*A61H 19/00* (2006.01)

(52) U.S. Cl.
CPC ..... *A61H 19/44* (2013.01); *A61H 2201/0153* (2013.01); *A61H 2201/1604* (2013.01); *A61H 2201/1685* (2013.01); *A61H 2201/1692* (2013.01)

(58) Field of Classification Search
CPC ................................ A61H 19/40; A61H 19/44
USPC ........................................ 600/38–41; 601/46
See application file for complete search history.

(56) References Cited

U.S. PATENT DOCUMENTS

| | | | | |
|---|---|---|---|---|
| 7,513,868 | B1 * | 4/2009 | Fontenot | A61H 19/44 600/38 |
| 8,313,424 | B2 | 11/2012 | Gabrielidis | |
| 8,672,832 | B2 | 3/2014 | Lee | |
| 9,668,934 | B2 * | 6/2017 | Pearson | A61H 19/44 |
| 2005/0228218 | A1 * | 10/2005 | Skidmore | A61H 19/44 600/38 |

* cited by examiner

*Primary Examiner* — John Lacyk
(74) *Attorney, Agent, or Firm* — Jason T. Daniel, Esq.; Daniel Law Offices, P.A.

(57) ABSTRACT

A sexual stimulation device includes a main body having a generally blunt first end, a top surface, a bottom surface, and a dildo that extends outward from the bottom surface of the main body. The dildo including a curved shaft that forms an obtuse angle. A flap is positioned along the bottom surface adjacent to the second dildo. One or more removable and reconfigurable handles are secured to the blunt first end of the main body.

18 Claims, 7 Drawing Sheets

FEMALE SEXUAL STIMULATION DEVICE

CROSS-REFERENCE TO RELATED APPLICATION

This application claims the benefit of U.S. application Ser. No. 14/713,600 filed on May 15, 2015, the contents of which are incorporated herein by reference.

TECHNICAL FIELD

The present invention relates generally to the field of sex toys, and more particularly to a female sex toy which can engage and stimulate the female G-spot.

BACKGROUND

The statements in this section merely provide background information related to the present disclosure and may not constitute prior art.

In general, sex toys are well known in the prior art. For example, there are many known dildos which function to stimulate the erogenous zones of the human body. These devices are typically used to recreate the act of sex, and require a user to repeatedly insert and remove the device within a body orifice such as the vagina and/or anus, for example.

Additionally, there are many other known stimulation devices which incorporate secondary features such as vibrating elements, heating elements, and/or shape manipulating elements, for example. Although these devices are useful for clitoral stimulation, they still rely on the movement of the device, and do little to stimulate the female G-spot which is located two to three inches up the anterior vaginal wall between the vaginal opening and the urethra.

In this regard, it has been discovered that a prolonged and constant pressure applied to the female G-spot typically results in vaginal orgasm. However, most females cannot easily access their G-spot with conventional dildos, owing to the relatively small shape of these devices, which lack an elongated handle. As such, many women are only able to experience stimulation of their G-spot when engaged in sexual activities with a partner. Unfortunately, during such activities, there is still the above described in-and-out movement which alternately stimulates and ignores this region.

Accordingly, it would be beneficial to provide a female sexual stimulation device that can be utilized alone, or with a partner, to apply targeted and constant pressure to the female G-spot, and that does not suffer from the drawbacks described above.

SUMMARY OF THE INVENTION

The present invention is directed to a female sexual stimulation device. One embodiment of the present invention can include a main body having a generally blunt first end, a top surface, a bottom surface, and a dildo that extends outward from the bottom surface of the main body. The dildo can include a curved shaft that forms an obtuse angle so as to position the tip member beneath the generally blunt first end of the main body. The invention can also include one or more handles that can be secured to the main body, so as to allow the device to be easily utilized alone or with a partner.

Another embodiment of the present invention can also include a flap member that is positioned adjacent to the second dildo. The flap member including a shape and size that is designed to spread the labia of a device user.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

Figure 1:
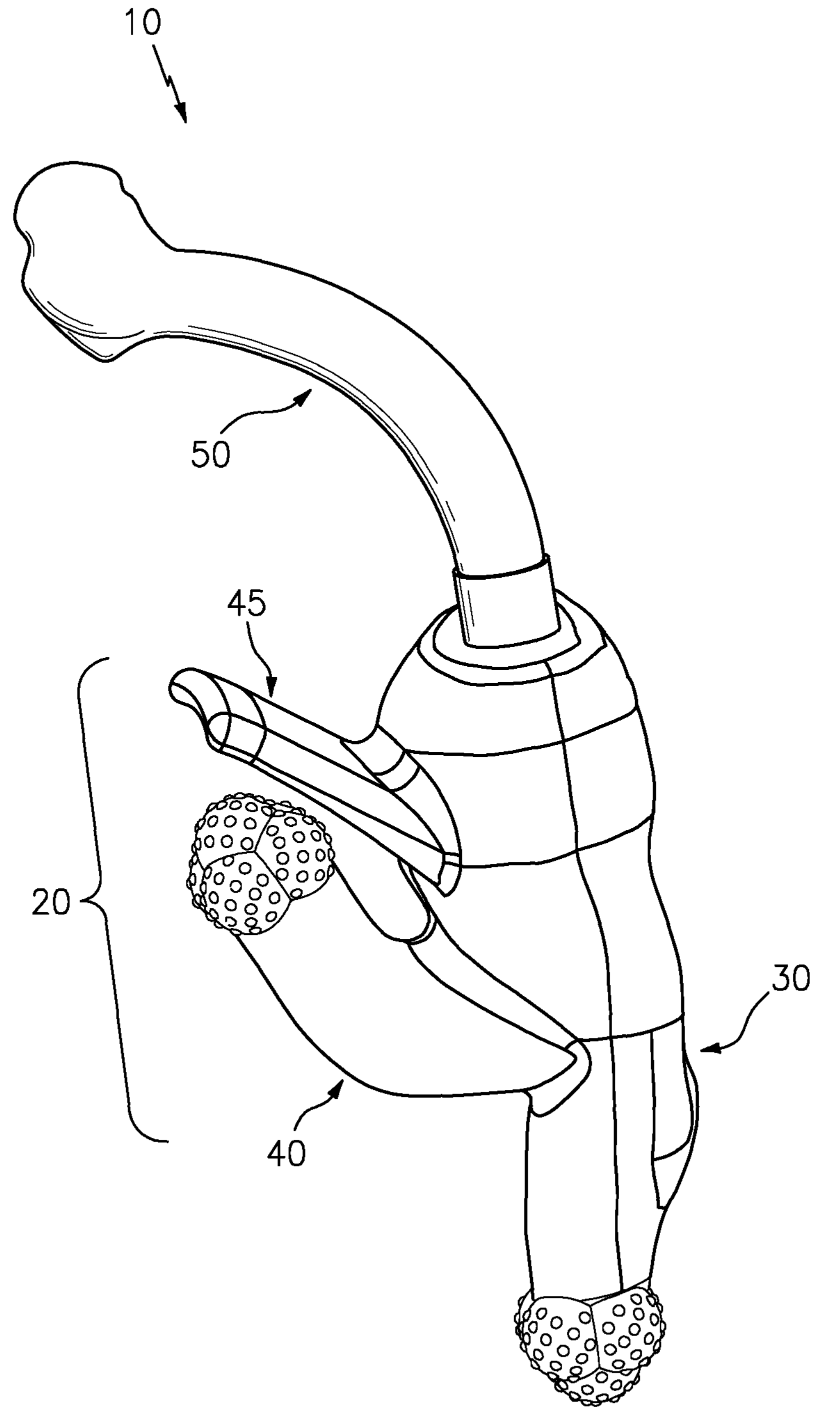
FIG. 1 is a perspective view of a female sexual stimulation device that is useful for understanding the inventive concepts disclosed herein.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

As described throughout this document the term "G-spot" shall be used generally to describe the female anatomy which is located two to three inches up the anterior vaginal wall between the vaginal opening and the urethra, as well as the entire clitoral organ and connected/connective tissue. Additionally, the term "removably secured," and derivatives thereof shall be used to describe a situation wherein two or more objects are joined together in a non-permanent manner so as to allow the same objects to be repeatedly joined and separated. Finally, the term "rotatably connected" and "rotatably secured" and all derivatives shall be used interchangeably to describe a situation wherein two or more objects are joined together in a manner that allows one or both of the objects to rotate about or in relation to the other object.

Identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 3.

Although described throughout this document as a device for engaging a female G-spot, the invention is not to be construed as limiting to any particular use or industry. As will be understood by those of skill in the art, the device can be configured for insertion into other orifices, and for stimulation of other body parts in both women and men. Moreover, although described with respect to a solo use and partner use, this is for illustrative purposes only, as all of the described functionality can be utilized by individuals acting alone or with a partner.

As such, FIGS. 1-7 illustrate various embodiments of a female sexual stimulation device 10 that is useful for understanding the inventive concepts disclosed herein. As shown, the device 10 can include, essentially, a sex toy 20 having one or more removable and reconfigurable handles 50.

As will be detailed below, the device has dual functionality, so as to engage the female G-spot with or without the aid of a partner. In this regard, the sex toy 20 can include a main body having any number of different shapes, weights and construction materials. In one embodiment, the main body 21 can include a semi-rigid construction having a generally blunt first end 21*a*, an elongated top surface 21*b*, a bottom surface 21*c*, and a pair of opposing side surfaces 21*d* and 21*e*.

Partner Use

Figure 2:
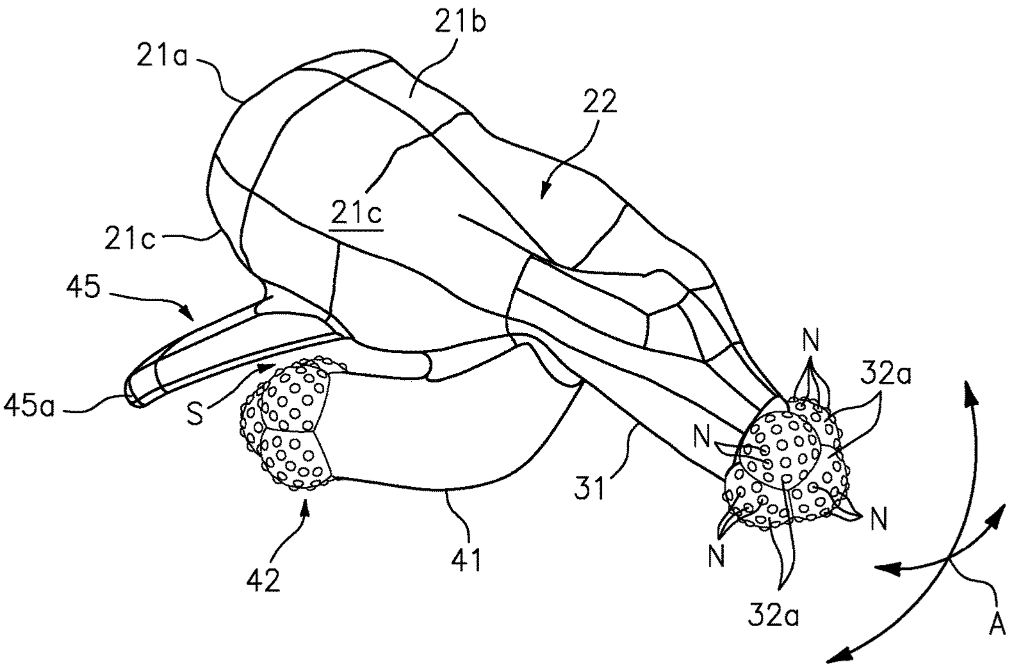
FIG. 2 is a side view of the female sexual stimulation device, in accordance with one embodiment of the invention.

As shown best in FIG. 2, the second end of the main body can form a first dildo 30 that is preferably used in conjunction with a partner. As shown, the first dildo is located opposite to the blunt first end 21*a*, and extends outward in a generally linear and/or slightly angled manner e.g., between 5 and 40 degrees. The first dildo is configured for insertion into an opening, such as a human vagina, and can include an elongated shaft 31 and distal tip member 32. In one embodiment, the distal tip member 32 can include a plurality of vertically and horizontally stacked orbs 32*a*, each of which include multiple nubs N extending outward therefrom in all directions.

In one embodiment, the toy 20 further includes a chin cup 22 having a generally curved indentation that is provided along the top surface of the main body 21*b* at a location adjacent to the first dildo 30. The indentation extends downward towards the bottom surface 21*c*, and functions as a cup for receiving the chin of a partner. In this regard, when the device is used with a partner, and the first dildo 30 is inserted within the vagina of the user, the cup 22 functions to align the partners' mouth with the external clitoris of the user to facilitate oral sex. Moreover, by providing an area having a shape and size that approximates the shape and size of a human chin, the chin cup 22 allows the partner to use their chin (in conjunction with, or in place of the handle) to manipulate the angle at which the first dildo is inserted within the vagina, and to increase and/or decrease the pressure imparted by the first head 32 against the G-spot.

Solo Use

Figure 3A:
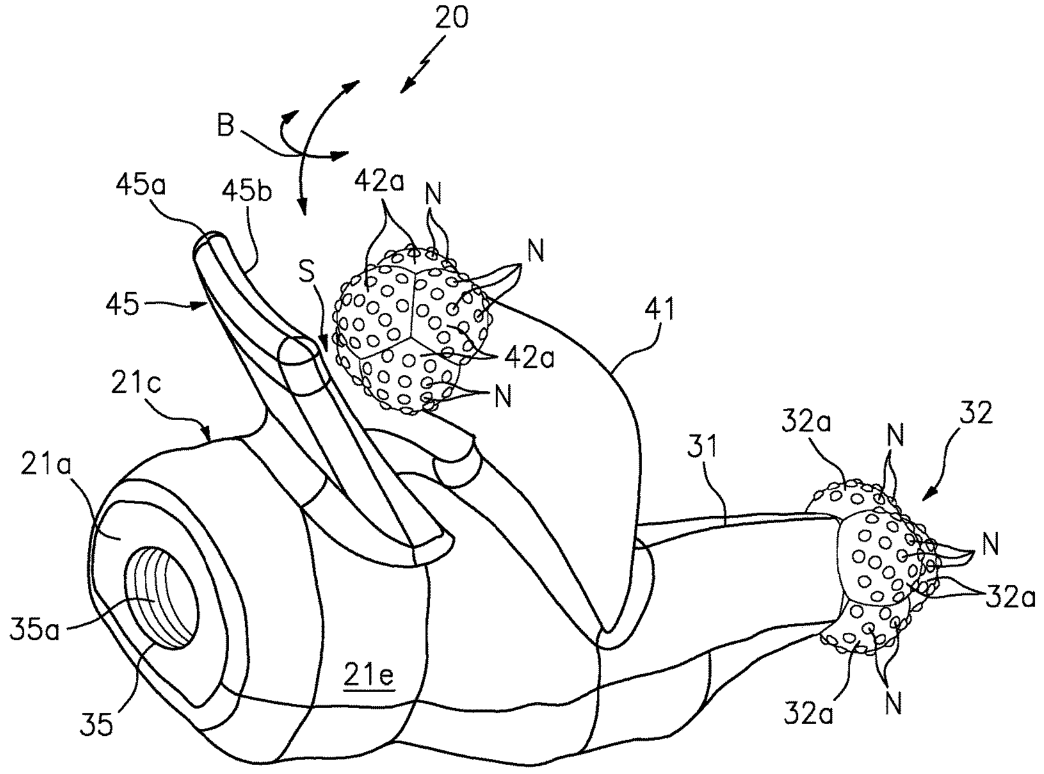
FIG. 3A is a bottom view of the female sexual stimulation device, in accordance with one embodiment of the invention.

As shown best in FIG. 3A, the device can also include a second dildo 40 that can be easily used without the aid of a partner (i.e., solo use). The second dildo can be oriented away from the first dildo 30, and is also configured for insertion into an opening, such as a human vagina. In this regard, the second dildo can include a generally curved shaft 41 that extends outward from the bottom surface of the main body 21*c* at a location beneath the chin cup 22. The curved section of the shaft forms an obtuse angle that extends and positions the second tip member 42 beneath the blunt first end 21*a*. In the illustrated embodiment, the distal tip member 42 can also include a plurality of vertically and horizontally stacked orbs 42*a*, each of which having multiple nubs N extending outward therefrom in all directions.

Figure 3B:
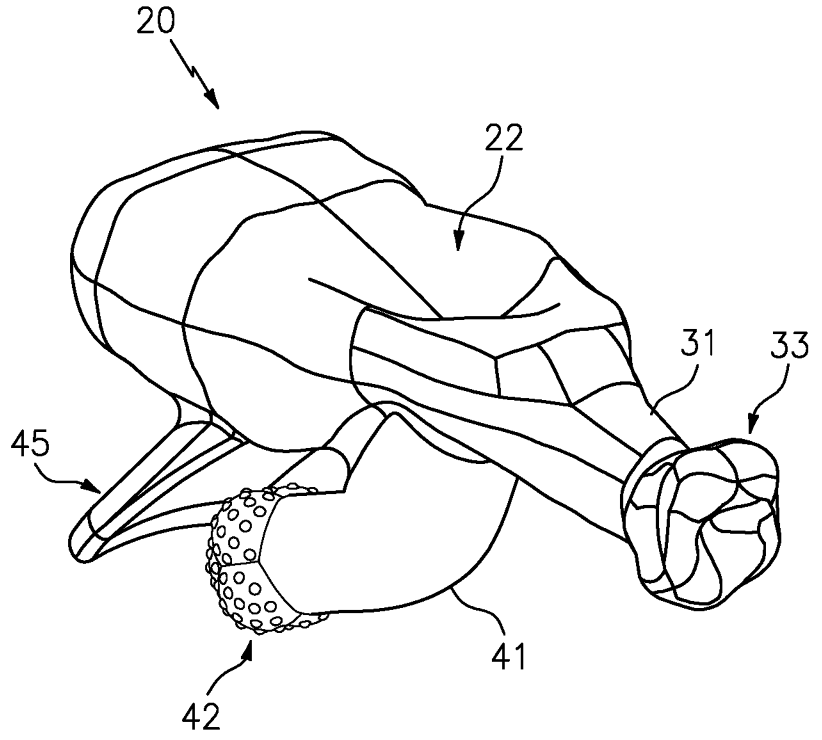
FIG. 3B is a side view of the female sexual stimulation device, in accordance with another embodiment of the invention.

Although the distal tip members 32 and 42 are described above as including essentially identical elements having a specific shape, size and features, this is for illustrative purposes only, as other distal tip members having any number of different shapes, sizes and features are also contemplated. For example, FIG. 3B illustrates another embodiment of the toy 20, wherein one of the dildos includes a distal tip member 33 having a central indentation 33*a* and a plurality of outward radiating and curved corner/edge members 33*b* that surround the central indentation. To this end, various embodiments of the device can be constructed so as to include distal tip members that are identical or different from each other.

As shown, an elongated flap member 45 can extend angularly from the bottom surface of the main body 21*c*. The flap 45 is positioned so as to leave a space S between itself and the second dildo 40, and includes a distal end 45*a* that extends beneath the blunt first end 21*a*. As shown, the flap can include a generally curved surface 45*b* that is adjacent to the space S.

Although dimensions are not critical, in the preferred embodiment, the flap 45 can include a length (e.g., measured from the bottom of the main body 21*c* to the distal end 45*a*) of between approximately 1 and 5 inches. Likewise, the space S can preferably include a distance of between approximately 0.25 and 1 inches. Of course, other lengths are also contemplated.

In operation, when the device 10 is used without a partner, the second dildo 40 can be positioned to enter the user's vagina, and can be inserted therein via an upward pulling motion on the handle. At this time, the flap 45 functions to engage and spread the user's labia, so as to allow the solo user to more easily insert the second dildo 40. Additionally, the flap functions to protect the labia and the pubic bone from inadvertent contact with the handle once the second dildo has been inserted.

As described herein, the first and second dildos 30 and 40 can each be constructed in accordance with known practices to include any number of different stiffness levels such as rigid, semi-rigid, or flexible, for example. In this regard, each of the dildos 30 and 40 can be constructed to allow the same to remain in a generally fixed position, to bend slightly (e.g., between 1 and 15 degrees) or to bend greatly (e.g., between 1 and 45 degrees), respectively. This bending movement can be in all directions, as shown by arrows A and B, however other stiffness levels and amounts of movements are also contemplated. Moreover, each of the shafts 31/41 and tip members 32/42 can be constructed to include identical shapes and sizes (e.g., length, width, diameter/girth, etc.,). Alternatively, each of the shafts 31/41 and/or tip members 32/42 can be constructed to include shapes and sizes that are not identical.

Returning to FIG. 3A, an aperture 35 can be centrally located along the first end 21*a* of the main body, and can include a plurality of threaded elements 35*a* which can engage complementary elements located on the below described handle.

Although described above as separate components, this is for illustrative purposes only, as the entire sex toy 20 can be constructed as one integral unit that is constructed from or coated with platinum-cure silicone rubber. Of course, any number of other materials commonly used for such devices, and which will be comfortable for the user are also contemplated. Several nonlimiting examples include various forms of rubber, plastics and/or silicone materials, for example.

Although the dimensions are not critical, it is preferred that each of the dildos 30 and 40 include a length from the main body of between approximately 2.5 and 3 inches. Such a feature will ensure that the tip member(s) are properly aligned with the G-spot when the device is in use. Additionally, as the device functions to impart a constant pressure onto the G-spot, and is not intended to be repeatedly inserted and removed, it is preferred that the main body be relatively heavy, as compared to traditional sex toys. In this regard, the main body can be constructed to include a preferred weight ranging between approximately 700 and 1000 grams. Of course, any number of other lengths and weights are also contemplated.

As noted above, the toy has functionality to accommodate use in either a solo capacity or with a partner. In this regard, the device can include any number of different handles, as described below with respect to FIGS. 4 and 5.

When the device is utilized in a solo capacity, it is beneficial to provide a longer handle 50, so as to provide the user with leverage when applying pressure onto the G-spot. Additionally, the longer handle can allow the user to easily manipulate the sex toy without having to bend or twist their body at an awkward angle.

Figure 4A:
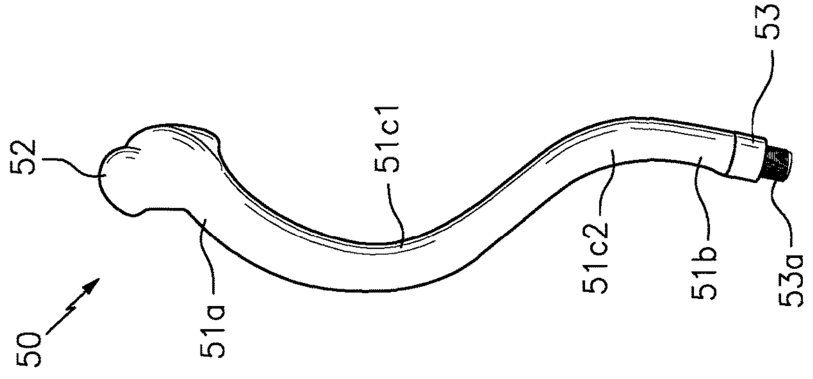
FIG. 4A is a top view of the handle of the female sexual stimulation device, in accordance with one embodiment of the invention.

As such, FIG. 4A illustrates one embodiment of a removable handle 50 for use with the above described toy 20, in a solo capacity. As shown, the handle 50 can include an elongated generally S-shaped shaft having a first end 51*a*, a second end 51*b*, and a pair of curved sections 51*c*1 and 51*c*2 that are disposed between the first and second ends. In one embodiment, a hand grip 52 is positioned along the first end, to aid a user in manipulating the device, and an adaptor 53 having a plurality of threaded elements 53*a* are disposed along the second end.

Figure 4B:
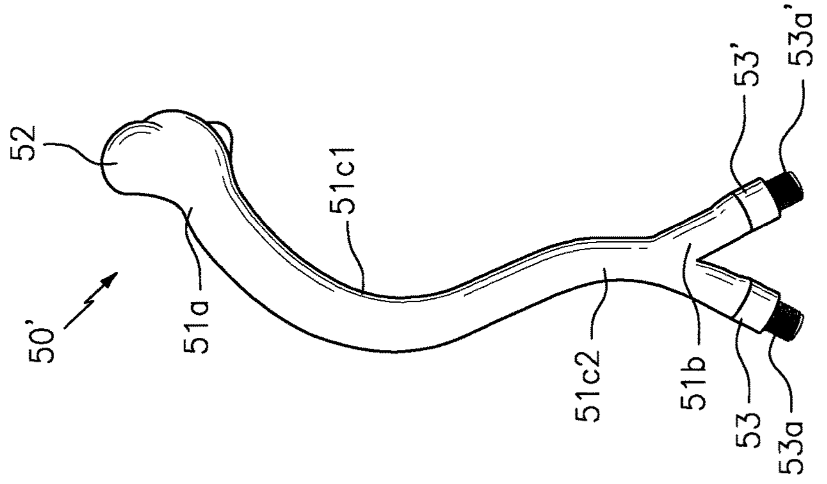
FIG. 4B is a top view of the handle of the female sexual stimulation device, in accordance with another embodiment of the invention.

FIG. 4B illustrates another embodiment of a long handle 50'. As shown, the handle 50' can also include an elongated generally S-shaped shaft having a first end 51*a*, a second end 51*b*, and a pair of curved sections 51*c*1 and 51*c*2 that are disposed between the first and second ends. In this embodiment, the handle also includes the hand grip 52 that is positioned along the first end, and further includes two adaptors 53 and 53' having a plurality of threaded elements 53*a* and 53*a*' respectively. The handle 50' can be utilized in two distinct ways. First, by providing two adaptors that are oriented approximately 45 degrees from another, the handle advantageously allows a user to secure a sex toy onto either adaptor, so as to provide the long handle at different angles. Secondly, by providing two adaptors, it becomes possible for the single handle to removably engage two separate sex toys 20, in order to allow two users to use the device simultaneously (wherein each user would follow the steps described above pertaining to solo use).

Although dimensions are not critical, in the preferred embodiment, the handles 50 and 50' can include a length (e.g., measured from the first end 51*a* to the second end 51*b*) of between approximately 8.5 and 18 inches. Of course, other lengths are also contemplated.

Figure 5:
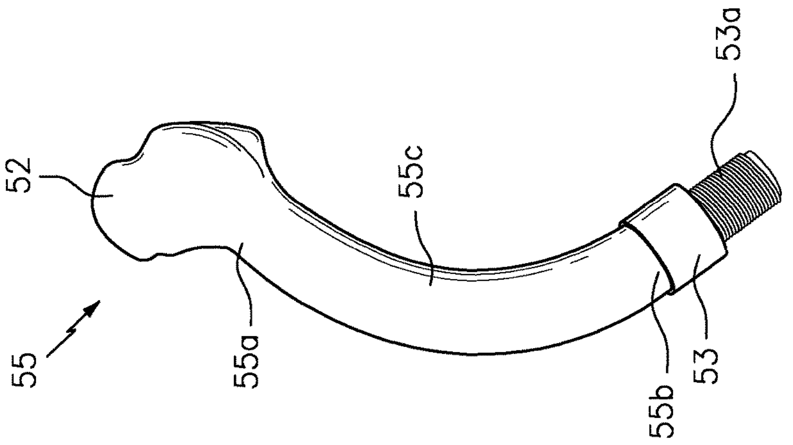
FIG. 5 is a top view of the handle of the female sexual stimulation device, in accordance with another embodiment of the invention.

Although the long handle 50 can be utilized in conjunction with a partner, other embodiments are also contemplated for providing a relatively short handle 55, that can allow the partner to easily manipulate the sex toy. As such, FIG. 5 illustrates another embodiment of a handle 55 for use when the above described toy 20 is used with a partner. As shown, the handle can include a generally short shaft member having a first end 55*a*, a second end 55*b*, and a single curved section 55*c* that is disposed between the first and second ends. In one embodiment, the above described hand grip 52 and threaded elements 53 are disposed along the first and second ends, respectively.

Although dimensions are not critical, in the preferred embodiment, the handle shaft 55 can preferably include a length (e.g., measured from the first end 55*a* to the second end 55*b* of between approximately 5 and 11 inches. Of course, other lengths are also contemplated.

As should be readily apparent, the threaded elements 53 can function to removably engage the complementary threaded elements 35*a* disposed within the first end 21*a* of the above described sex toy 20 via a twisting motion. In this regard, the handles 50, 50' and 55 can be secured to the toy 20, in a manner that allows the first end 51*a* and the hand grip 52 to twist 360 degrees relative to the toy (see arrows C in FIGS. 6 and 7). Such a feature, combined with the curved section(s) allow a user to easily use and manipulate the handle with either their left or right hand.

Threaded elements having lands and grooves for securing complementary objects together via a twisting motion are extremely well known, and no further description will be provided. Of course, the device is not limited to the use of threaded elements, as any number of other known devices capable of removably securing the handle to the device and/or rotatably securing the handle to the device are also contemplated. One such example, includes a flange and pin, for example.

Figure 6:
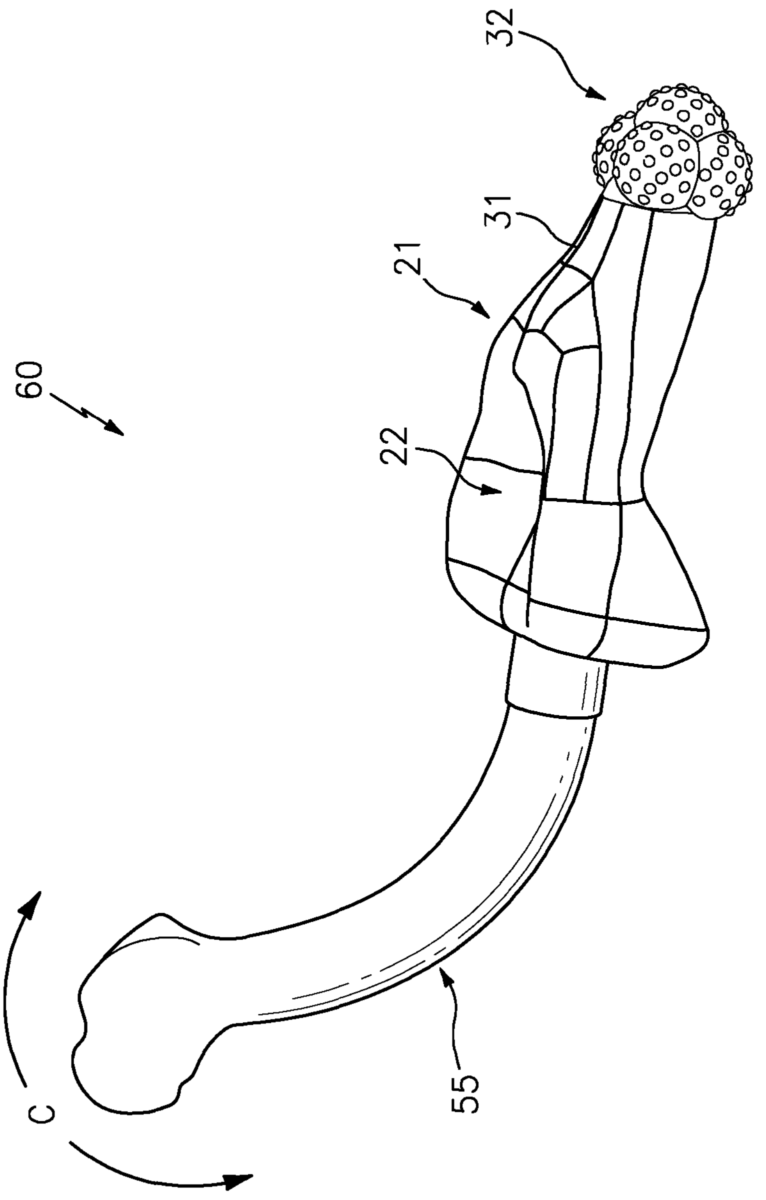
FIG. 6 is a side view of the female sexual stimulation device, in accordance with another embodiment of the invention.

FIG. 6 illustrates an alternate embodiment of a female sexual stimulation device 60 that is constructed for use with a partner. As shown, the device 60 can include only the above described short handle 55, main body 21, chin cup 22, and first dildo having the shaft 31 and tip member 32. Of course, this embodiment is not limited to use with a partner, as it is certainly possible for a user to use device 60 alone.

Figure 7:
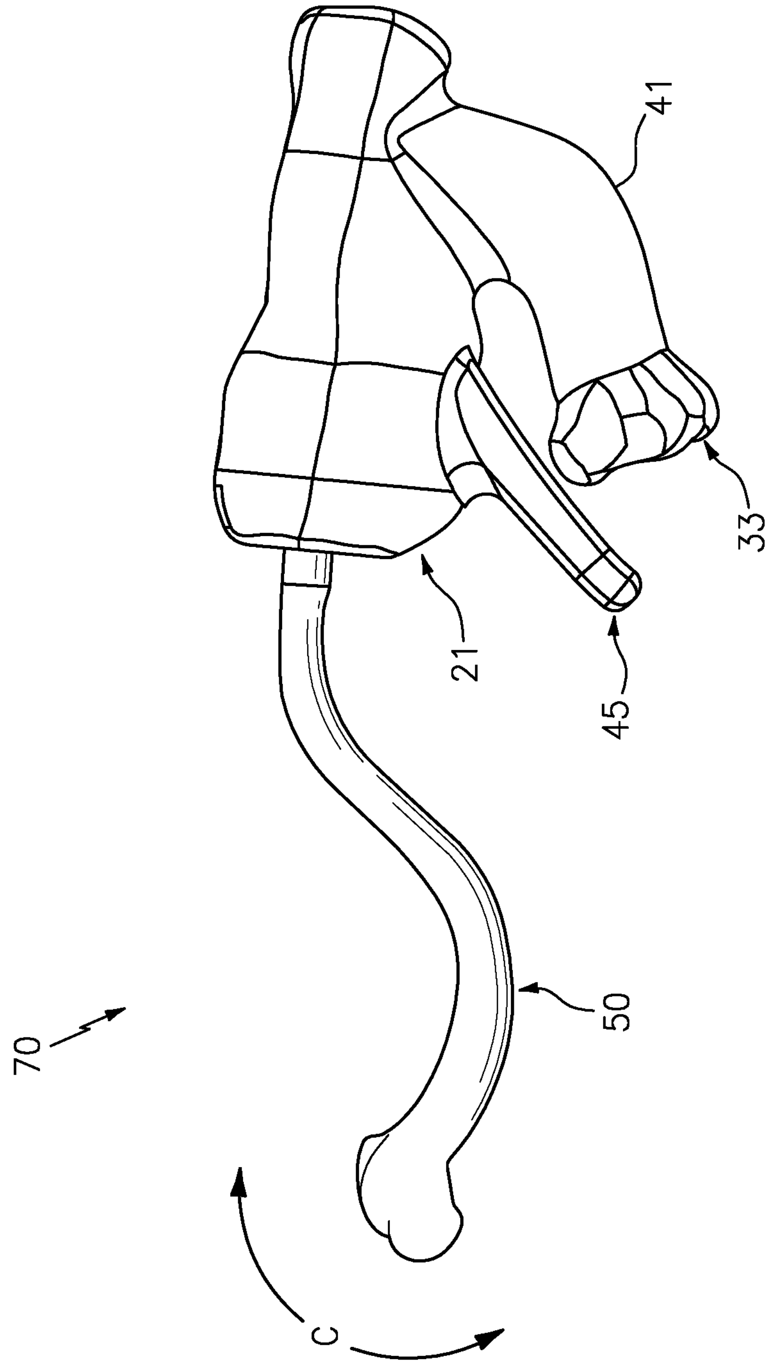
FIG. 7 is a side view of the female sexual stimulation device, in accordance with another embodiment of the invention.

FIG. 7 illustrates another embodiment of a female sexual stimulation device 70 that is constructed for solo use. As shown, the device 70 can include the above described main body 21, flap member 45, a handle, and the second dildo having the shaft 41 and distal tip member 33. The device 70 can be utilized in the above described manner, and is specifically adapted for solo use.

Accordingly, the above described female sexual stimulation device can be utilized alone or with a partner, to apply targeted and constant pressure to the female G-spot, in a unique manner. As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A female sexual stimulation device, comprising:

a main body that includes a generally blunt first end, a top surface, and a bottom surface;

a dildo that extends outward from the bottom surface of the main body, said dildo including an elongated shaft and a distal tip member, wherein the shaft forms an obtuse angle that positions the distal tip member beneath the generally blunt first end of the main body;

at least one handle that is secured to the blunt first end of the main body; and an elongated flap member that extends angularly from the bottom surface of the main body in a direction generally parallel with the dildo, wherein said flap member is separated from the dildo by a first space.

2. The device of claim 1, wherein the at least one handle is removably secured to the main body.

3. The device of claim 1, wherein the flap member includes a curved surface that functions to spread a female labia during device usage.

4. The device of claim 1, wherein the first space is between approximately 0.25 and 1 inch.

5. The device of claim 1, wherein the distal tip member includes a plurality of vertically and horizontally stacked orbs, each having a plurality of nubs extending outward therefrom.

6. The device of claim 1, wherein the distal tip member includes a plurality of outward radiating and curved corner sections that are disposed about a central indentation.

7. A female sexual stimulation device, comprising:

a main body that includes a generally blunt first end, a top surface, and a bottom surface;

a dildo that extends outward from the bottom surface of the main body, said dildo including an elongated shaft and a distal tip member, wherein the shaft forms an obtuse angle that positions the distal tip member beneath the generally blunt first end of the main body;

at least one handle that is secured to the blunt first end of the main body;

an aperture that is disposed along a central portion of the blunt first end; and a plurality of threaded elements that are disposed along an inside portion of the aperture.

8. The device of claim 7, wherein the at least one handle includes:

a long handle having an elongated, generally S-shaped shaft having a first end, a second end, and a pair of curved sections that are disposed between the first and second ends;

a hand grip that is positioned along the first end; and an adaptor having a plurality of complementary elements that are disposed along the second end of the handle shaft, said complementary elements being configured to engage the threaded elements within the aperture of the main body.

9. The device of claim 8, further comprising:

a second adaptor having a second plurality of complementary elements that are disposed along the second end of the handle shaft, said second plurality of complementary elements being configured to engage the threaded elements within the aperture of the main body.

10. The device of claim 8, wherein said handle is configured to twist 360 degrees relative to the main body.

11. The device of claim 8, wherein said handle includes a length of between approximately 8.5 and 18 inches.

12. The device of claim 7, wherein said at least one handle includes:

a short handle having a shaft with a first end, a second end, and a single curved section that is disposed between the first and second ends;

a hand grip that is positioned along the first end; and an adaptor having a plurality of complementary elements that are disposed along the second end of the handle shaft, said complementary elements being configured to engage the threaded elements within the aperture of the main body.

13. The device of claim 12, wherein said handle is configured to twist 360 degrees relative to the main body.

14. The device of claim 13, wherein said handle includes a length of between approximately 5 and 11 inches.

15. A female sexual stimulation device, comprising:

a main body that includes a generally blunt first end, a top surface, and a bottom surface;

a dildo that extends outward from the bottom surface of the main body, said dildo including an elongated shaft and a distal tip member, wherein the shaft forms an obtuse angle that positions the distal tip member beneath the generally blunt first end of the main body; and at least one handle that is secured to the blunt first end of the main body, wherein each of the at least one handle is rotatably secured to the blunt first end of the main body.

16. The device of claim 1, wherein the dildo includes a length a length from the main body of between approximately 2.5 and 3 inches, said length functioning to position the distal tip member against a female G-spot so as to apply a constant pressure thereon.

17. The device of claim 1, wherein the elongated shaft of the dildo is curved.

18. The device of claim 1, wherein the main body includes a weight of between approximately 700 and 1000 grams.

* * * * *